(12) United States Patent
de Bruijn

(10) Patent No.: US 6,677,507 B2
(45) Date of Patent: Jan. 13, 2004

(54) TALL FESCUE VARIETY HAVING RHIZOMES

(75) Inventor: Jacobus de Bruijn, Mas Grenier (FR)

(73) Assignee: Barenbrug USA, Inc., Tangent, OR (US)

( * ) Notice: Subject to any disclaimer, the term of this patent is extended or adjusted under 35 U.S.C. 154(b) by 0 days.

(21) Appl. No.: 10/066,345

(22) Filed: Jan. 30, 2002

(65) Prior Publication Data

US 2003/0172415 A1 Sep. 11, 2003

(51) Int. Cl.$^7$ .................................................. A01H 5/00
(52) U.S. Cl. ........................................ 800/320; Plt./388
(58) Field of Search ................................. 800/320, 278, 800/294, 293, 200; Plt./388

(56) References Cited

PUBLICATIONS

Cultural factors for minimizing bermudagrass invasion into tall fescue turf. Brede, A.D. Agronomy journal Nov./Dec. 1992. Vol 84 No. 6. pp. 919–922.*
Jain and Jain, "Transgenic Strategies for Genetic Improvements of Basmati Rice," *Indian J. Exp. Biol. 38*:6–17 (2000).
Bouton et al., "Field Screening for Rhizome Number in Tall Fescue," *Crop Sci. 32*:686–689 (1992).
Bouton et al., "Tall Fescue Rhizome Production as Influenced by Bermudagrass Competition and Cutting Frequency," *Agron. J. 81*:220–223 (1989).
De Battista et al., "Greenhouse Evaluation of Tall Fescue Genotypes for Rhizome Production," *Crop Sci. 30*:536–541 (1990).
Jernstedt et al., "Anatomy, Morphology, and Growth of Tall Fescue Rhizomes," *Crop Sci. 25*:539–542 (1985).
Wilkinson et al., "Compatability of Tall Fescue and Coastal Bermudagrass as Affected by Nitrogen Fertilization and Height of Clip," *Agron. J. 60*:359–362 (1968).

* cited by examiner

*Primary Examiner*—Bruce R. Campell
*Assistant Examiner*—Annette H. Para
(74) *Attorney, Agent, or Firm*—Klarquist Sparkman, LLP

(57) ABSTRACT

A tall fescue variety known as breeder's code Bar Fa 08PB and seed used to produce the grass are provided. Methods of using the grass plant and the seed are also provided. This grass is suitable for use in turf (lawns, pastures, golf courses, sod, and other areas where excellent turf quality is desired) and forage pastures.

54 Claims, 1 Drawing Sheet

TALL FESCUE VARIETY HAVING RHIZOMES

FIELD

This disclosure relates to a tall fescue grass having rhizomes that has a superior turf quality compared to other known tall fescues with rhizomes. One embodiment of this grass is known as breeder's code Bar Fa 08PB.

BACKGROUND

Tall fescue (*Festuca arundinacea* Schreb.) is a short- to medium height, cool-season, perennial grass used extensively for pasture, hay, and turf, that has smooth, soft, bright green leaves with arrow-shaped tips. Tall fescue is an excellent low-maintenance turfgrass, due to its ability to tolerate drought and shade (See *Tall Fescue*, Edited by Buckner and Bush, Published by the American Society of Agronomy, Crop Science Society of America, and Soil Science Society of America. ASA Monograph Number 20. 1979. ISBN 0-89118-057-5). However, tall fescue has a limited use in areas which experience extreme high or low temperatures, such as the Southeastern United States. In addition, a major problem with tall fescue it its slow recovery from injury (such as overgrazing and overmowing) and its tendency to become clump if not overseeded.

Rhizomes are underground stems that allow grasses to spread and form a close-knit sod that regrows after injury. Rhizomes benefit plants by storing carbohydrates, which increases heat and wear resistance of the plant, and allows the plant to spread and compete better in a sward. Rhizomes also provide growing points under the surface of the soil, where they are better protected from temperature, prolonged drought, and overgrazing. Therefore, it is desirable to increase rhizome production in tall fescue to promote persistence under conditions of stress, such as extremes in temperature. This may allow tall fescue plants to perennate in areas now considered marginal for its adaptation and use.

Although others rhizomatous tall fescue plants have been described, the tall fescues described have not been ideal. Genotypic variability for rhizome production has been documented, and no genotype x location interaction was reported for the trait. For example, De Battista and Bouton (*Crop Science*, 30:536–540, 1990) describe a tall fescue which took at least seven months of growth before rhizome expression occurred under greenhouse conditions. Furthermore, there was no correlation between the top rhizome producers in the greenhouse to the top rhizome producers in the field. Studies by Bouton et al. (*Agron J.* 81:220–23, 1989) demonstrated that bermudagrass competition depressed rhizome production, but that even the most rhizomatous genotype 83-29 produced only 0.2 to 0.4 rhizomes per tiller, and the plants only spreading up to 0.3 m per year (Cowan *Adv. Agron.* 8:293–320, 1956).

Therefore, there is a need to identify a tall fescue having rhizomes which can grow in subtropical climates and the southern portion of the transition zone, recover quickly from injury, and reproducibly produce high-quality turf.

SUMMARY

Herein disclosed is a tall fescue variety known as breeder's code Bar Fa 08PB that is different from all known varieties of tall fescue plants. In one embodiment, mature Bar Fa 08PB plants reach a height from about 90 cm to about 135.5 cm tall, produce about 1 to about 10 rhizomes per plant, which are from about 1 cm to about 33 cm in length, have a high rust-resistance tolerance, and/or have a high turf quality rating when the plants are about one year in age. In another embodiment, Bar Fa 08PB plants tolerate mowing better than other tall fescues having rhizomes, such as Torpedo (variety).

At least 2500 seeds of Bar Fa 08PB were deposited with The American Type Culture Collection (ATCC, Manassas, Va.; ATCC Deposit No. PTA-3825) on Nov. 5, 2001 under the Budapest Treaty. These seeds will be irrevocably and without restriction released to the public upon the issuance of a patent. Therefore, these seeds are known and readily available to the public. In one embodiment, the disclosure provides grass seed deposited as ATCC No: PTA-3825.

In one embodiment, the disclosure provides tall fescue plants having the morphological and physiological characteristics of Bar Fa 08PB. Also disclosed are seeds of such plants, progeny of such plants, and vegetative sprigs or clones of such plants. In another embodiment, the disclosure provides grass plants having the genotype of Bar Fa 08PB.

The disclosure also encompasses tall fescue plants that are produced by crossing Bar Fa 08PB with other grass varieties. Also disclosed are seeds resulting from such a cross, grass plants grown from such seeds, and vegetative sprigs or clones from such a cross. In one embodiment, the seeds resulting from the cross are part of a seed mixture.

In another embodiment, the disclosure provides a method of producing grass seed, including planting seed from Bar Fa 08PB under conditions that result in the germination of the seed, growth of grass plants and setting of progeny seed, and then harvesting the progeny seed. Also disclosed is grass seed produced by this method, as well as grass seed mixtures including such grass seed.

Also disclosed is a method of producing a grass plant which includes crossing a grass plant produced from Bar Fa 08PB with at least one other grass plant to produce at least one seed, harvesting the seed, and germinating the seed to produce at least one progeny grass plant. Included in the disclosure are grass plants produced using this method, as well as a vegetative sprig or clone of the grass plant.

The grass plants disclosed herein can be planted in a variety of areas, for example in areas where turf is desired. Examples include, but are not limited to: golf courses, for example golf course fairways and roughs; lawns; athletic fields, such as football fields, baseball fields, soccer fields, lacrosse fields, and tennis courts; parks; and pastures, such as areas for animal grazing. In one embodiment, the grass plants disclosed herein are used for erosion control, such as in grass waterways. In another embodiment, the grass plants disclosed herein are adapted to low mowing.

The disclosure also includes sod or animal feed, such as hay, which includes the grass plants disclosed herein. The sod can be planted in any area where grass plants are desired, such as the areas listed above.

In one embodiment, the grass plants disclosed herein include one or more transgenes.

Endophytes associated with the disclosed grass plants and seeds are disclosed. In one example, endophytes produce one or more alkaloids, such as lolitrem B and/or ergovaline at levels not toxic to livestock. In particular examples, endophytes produce less than about 300 ppb ergovaline, such as less than about 100 ppb, 80 ppb, or 60 ppb, such as about 55 ppb of ergovaline. Alternatively or in addition, endophytes produce less than 1800 ppb of lolitrem B, such as less than about 1000 ppb, 750 ppb, 500 ppb, 300 ppb, 200 ppb or 100 ppb of lolitrem B.

The foregoing and other objects, features, and advantages of the new tall fescue variety described herein will become more apparent from the following detailed description of several embodiments, which proceeds with reference to the accompanying figure.

DETAILED DESCRIPTION OF SEVERAL EMBODIMENTS

EXAMPLE 1

Figure 1:
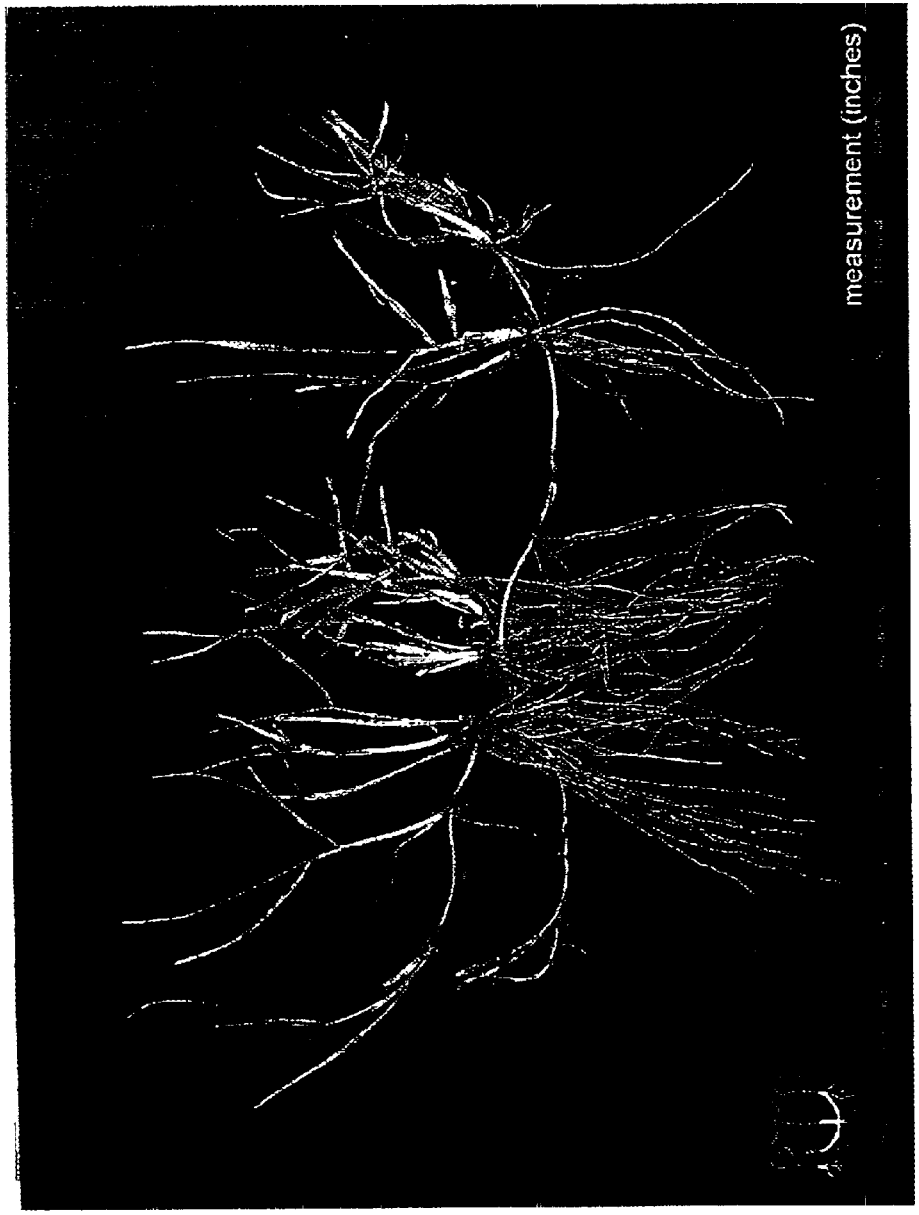
FIG. 1 is a digital image of an exemplary Bar Fa 08PB showing the length of rhizomes.

Origin and Breeding History of Tall Fescue Variety Bar Fa 08PB

The Bar Fa 08PB (*Festuca arundinacea*) variety was developed by Barenbrug U.S.A., Inc. at the Barenbrug Research Station in Mas Grenier, France. This variety was developed for its rhizomatous phenotype, and its ability to produce high-quality turf. This variety, because of its rhizomatous spreading, is useful for growing tall fescue sod for turf.

The breeding program was designed to breed and select for a tall fescue cultivar adapted to marginal lawn conditions in subtropical climates and the southern portion of the transition zone. Such tall fescue plants should mix better with warm season lawn species and growing sod where Kentucky bluegrass (*Poa pratensis* L.) is not adapted. The rhizome trait in tall fescue should impart better persistence and competitive ability in area marginal for its adaptation or in mixed swards (Bouton et al., *Agron J.* 81:220–23, 1989).

The selection of Bar Fa 08PB began during a collection trip in 1993 of ecotypes of rhizomatous tall fescue found in Northwest Portugal which were randomly pollinated the same year with a genepool of American and European tall fescue selections. To increase the success in this crossing, flowers of the grass were inspected daily, and the pollen of the father-lines was moved to the flowers of the mother-lines at the appropriate time.

The F1 of 26 plants were planted in Mas grenier, France. From these 26 plants, 24 harvested F2 isolations were obtained in 1994. Due to the very low seed set, only a small turf trial was realized in Mas Grenier in 1995, and only four lines showed promising turf performance. The original plants from this collection were also planted in a turf trial, but none survived.

After planting the four lines which demonstrated promising turf performance in isolation, one line did not show enough aggressiveness and another yielded too little seed. The remaining two lines were crossed and harvested as Bar Fa 08PB in 1998. This seed was used to harvest nucleus seed in 1999, which delivered the breeder seed of ATCC PTA-3825. This new harvest yielded better then the former F2. Bar Fa 08PB has been tested and compared to other tall fescues, such as the creeping cultivar Torpedo, in a variety of trial fields in France, Italy and the USA (North Carolina) as described below.

Seed propagation is limited to three generations of increase from breeder seed: one each of foundation, registered and certified. Breeder seed is maintained at Barenbrug, U.S.A, Inc., in Oregon. Bar Fa 08PB is a stable and uniform variety. No off-types or variants have been observed in the reproduction or multiplication of this variety from the breeder seed nursery to the foundation field.

EXAMPLE 2

Seed Deposits

Seeds of the tall fescue variety Bar Fa 08PB were deposited with the ATCC (Manassas, Va.) under the Budapest Treaty on Nov. 5, 2001 under accession number PTA-3825. The variety is also maintained at, and available from, Barenbrug U.S.A., Inc., P.O. Box 239, Tangent, Oreg. 97389.

EXAMPLE 3

Seedling Vigor and Turf Quality

The following growth characteristics were observed for Bar Fa 08PB plants that were approximately one or two years old, grown in seeded turf plots in Mas Grenier, France (Table 1), Vicenza, Italy (Table 2), or the Sandhills Research Station at the North Carolina State University (NCSU), North Carolina, USA (Table 3). Variations on these measurements, or any other measurement disclosed herein, may be observed for plants of differing ages, grown in other locations, grown under different prevailing weather conditions (for example variations in rainfall, temperature, and/or photoperiod), grown at different times of the year, mowing conditions, and/or grown in different soil.

Tall fescue seeds were sown in September 1999 at a seed quantity of 150 kg/ha, over three plots, each 0.75 square meters, in Mas Grenier, France. Rebel II (variety) seeds were obtained from ABT, USA. Torpedo (variety) seeds were obtained from Agriseeds, New Zealand.

The information provided in Table 1 relating to seedling vigor, snow mold resistance, persistence and turf quality (TQ) ratings (seasonal density, genetic color, and leaf texture) is derived from various turf trials. These data are expressed in numbers ranging from 1–9, with 1 representing low vigor, low snow mold resistance (diseased), low ground cover, or low TQ, and 9 representing desirable vigor, high mold resistance (no disease), high ground cover, and high turf quality.

TABLE 1

Growth Characteristics in Mas Grenier, France*

| Variety | Ground Cover[a] | Snow Mold resistance[a] | Avg. Ground Cover[b] | Winter TQ[c] | Summer TQ[d] | Average TQ[e] |
|---|---|---|---|---|---|---|
| Rebel II | 7.7 | 8 | 7.7 | 4.7 | 5.7 | 5.1 |
| Bar Fa 08PB | 8 | 5.7 | 4.8 | 4.7 | 4.3 | 4.3 |
| Torpedo | 6.3 | 6.3 | 1.8 | 1.3 | 1.3 | 1.2 |
| cv.(variet)[$] | 2.9 | 4.9 | 9.8 | 16.8 | 5.3 | 4.9 |
| LSD (.05)[#] | 0.7 | 1.1 | 1.8 | 2.3 | 0.7 | 0.6 |
| Avg or 100[1] | 7.3 | 6.5 | 5.2 | 3.9 | 4.1 | 3.7 |

*Mean measurements taken on a tall fescue turf trial on:
[a]Feb. 26, 1999;
[b]Feb. 4, 1999 and May 10, 1999;
[c]Feb. 29, 2000;
[d]Aug. 8, 2000;
[e]Feb. 29, 2000, Jun. 2, 2000, Aug. 23, 2000, Nov. 30, 2000.
[$]cv (coefficient of variation): Expresses the experimental error as percentage of mean; thus, the higher the cv value, the lower the reliability of the experiment.
[#]To determine statistical differences among entries, subtract one entry's mean from another entry's mean. Statistical differences occur when this value is equal to or larger than the corresponding L.S.D. value.
[1]To calculate the average, the value for each entry was added, then divided by the total number of entries.

A similar study was conducted in Vicenza, Italy as follows. Tall fescue seeds were sown in September 1999 at a seed quantity of 160 kg/ha, over two plots, each 1 square meter. Southern Choice (variety) seeds were obtained from Southern States, USA. Bonsai (variety) seeds were obtained from TMI, USA. Plantation (variety) seeds were obtained from Pennington Seed Company, USA. Barlexas II (variety) seeds were obtained from Barenbrug USA. Torpedo (variety) seeds were obtained from Agriseeds, New Zealand.

The information provided in Table 2 relating to establishment and TQ ratings (seasonal density, genetic color, and leaf texture) is derived from turf trials in Vicenza, Italy. These data are expressed in numbers ranging from 1–9, with 1 representing low establishment or low TQ, and 9 representing high establishment and high turf quality. Establishment is the combination of seedling vigor and rapidity of groundcover in the first three months after planting. Statistical analysis was performed as described above in Table 1.

TABLE 2

Growth Characteristics in Vicenza, Italy*

| Variety | Average Establishment[a] | Summer TQ[b] | Average TQ[c] |
|---|---|---|---|
| Southern Choice | 6.8 | 6 | 7 |
| Bonsai | 6.3 | 5.5 | 6.9 |
| Plantation | 6.5 | 6 | 6.8 |
| Barlexas II | 6.8 | 5.5 | 6.8 |
| Bar Fa 08PB | 6.8 | 5 | 5.8 |
| Torpedo | 6.5 | 3.5 | 4.8 |
| c.v. = . | 7 | 10.5 | 4.4 |
| LSD (0.05) = | 1.3 | 1.7 | .8 |
| Avg. or 100= | 6 | 5.2 | 6.2 |

*Mean measurements taken on a tall fescue turf trial on:
[a]three measurements taken on Oct. 23, 1999, Nov. 23, 1999, and Nov. 30, 1999;
[b]Aug. 18, 2000;
[c]eight measurements taken between Jan. 11, 2000 and Oct. 5, 2000.

A similar study was conducted at the Sandhills Research Station at NCSU, as follows. Tall fescue seeds were sown in the fall of 1999 at a seed quantity of 250 kg/ha, over three plots, each 1 square meter. Millenium (variety) seeds were obtained from TMI, USA, and Barlexas II (variety) seeds obtained from Barenbrug USA. The information provided in Table 3 relating to TQ ratings (seasonal density, genetic color, and leaf texture), winter color, density, and brown patch tolerance (that is, tolerance to *Rhizoctonia solani*, for example see Tani and Beard, *Color Atlas of Turfgrass diseases*, ISBN 1-57504-021-2), is derived from turf trials at the Sandhills Research Station at NCSU. These data are expressed in numbers ranging from 1–9, with 1 representing low TQ, poor winter color, low density, and low tolerance to brown patch (diseased), and 9 representing good winter color, high density, high brown patch tolerance (no disease) and high turf quality. Statistical analysis was performed as described above in Table 1.

TABLE 3

Growth Characteristics at the Sandhills Research Station at NCSU*

| Variety | Average TQ[a] | Winter Color[b] | Density[c] | Brown Patch Tolerance[d] |
|---|---|---|---|---|
| Millenium | 6 | 4.7 | 8.7 | 8.7 |
| Barlexas II | 5.1 | 4 | 9 | 9 |
| Bar Fa 08PB | 4.7 | 5.3 | 7.7 | 7.7 |
| c.v. = . | 5.8 | 5.1 | 8.8 | 4.6 |
| LSD (0.05) = | 1.2 | 0.9 | 1.8 | 1.5 |
| Avg. or 100 = | 5.3 | 4.7 | 5.1 | 8.4 |

*Mean measurements taken on a tall fescue turf trial on:
[a]in 2001;
[b]Feb. 15, 2001;
[c]May 9, 2001;
[d]Jun. 11, 2001.

Therefore, as shown in Tables 1–2, the Bar Fa 08PB variety has a superior turf quality to other known tall fescues, including tall fescues known to have rhizomes such as Torpedo. Table 3 shows that the Bar Fa 08PB variety has a similar turf quality as other tall fescues which do not have rhizomes.

EXAMPLE 4

Morphological and Rhizome Characteristics

Field trials were conduced to compare morphological and rhizome characteristics of the Bar Fa 08PB variety to currently used tall fescue grass varieties.

Seeds from nine different tall fescue varieties were sown in greenhouse potting medium in October 2000. After germination, the seedlings were transplanted into plug trays in November 2000. Seedlings were grown in the greenhouse until the plugs were filled with roots. At that time, December 2000, the plug seedlings were transplanted in a field nursery near Albany, Oreg. The seedlings were transplanted two feet apart. Sixty seedlings from each variety were grown in this field nursery. The field nursery was maintained with crop management practices used for grass seed production systems in the region. In mid July 2001, the following morphological characteristics were measured: (1) plant height; one measurement per plant; (2) flag leaf height (the flag leaf is the highest leaf on a grass stem); three measurements per plant on different tillers; (3) flag leaf blade length; three measurements per plant on different tillers; (4) flag leaf blade width; three measurements per plant on different tillers; (5) panicle length; three measurements per plant on different tillers; (6) tiller leaf width; one measurement per plant; (7) tiller leaf length; one measurement per plant; (8) first internode length; one measurement per plant; (9) peduncle length; one measurement per plant; (10) panicle height; one measurement per plant; (11) rust tolerance: one visual observation per plant.

The trial consisted of commercially available cultivars and the Bar Fa 08PB variety. All seeds listed in Tables 4–9, except Bar Fa 08PB and Torpedo, were obtained from Regional Plant Introduction Station, Washington State University, United States Department of Agriculture, Agricultural Research Service, 59 Johnson Hall, P.O. Box 646402, Pullman, Washington, USA 99164-6402.

Tables 4–6 show comparisons of several morphological characteristics of the Bar Fa 08PB variety with other tall fescue varieties. Statistical analysis was performed as described above. Means followed by same letter do not significantly differ.

TABLE 4

Morphological Measurements of Tall Fescues.

| Character Rated Rating Data Type Rating Unit Variety | Flag Leaf Height cm | Leaf Blade Length cm | Leaf Blade Width mm |
|---|---|---|---|
| Bonsai | 24.97 e | 6.51 d | 5.31 b |
| Bonanza | 42.26 bc | 12.34 a | 7.1 a |
| Bar Fa 08PB | 46.5 b | 11.1 abc | 6.4 a |
| Kentucky 31 Endo+ | 61.22 a | 12.16 ab | 6.81 a |
| Rebel II | 40.77 bc | 11.7 abc | 6.62 a |
| Rebel Jr | 28.57 e | 9.71 c | 6.05 ab |
| Shortstop | 37.32 cd | 10.41 abc | 6.51 a |
| Silverado | 32.13 de | 10.08 bc | 6.67 a |
| Torpedo | 40.87 bc | 12.12 ab | 6.06 ab |
| LSD (0.05) | 6.973 | 1.881 | 0.942 |
| Standard Deviation | 4.028 | 1.087 | 0.544 |
| CV | 10.22 | 10.18 | 8.51 |

TABLE 5

Morphological Measurements of Tall Fescues.

| Character Rated Rating Data Type Rating Unit Variety | Panicle Length cm | Heading* Day (Julian date) |
|---|---|---|
| Bonsai | 13.19 f | 145.7 bc |
| Bonanza | 22.47 bc | 150.2 a |
| Bar Fa 08PB | 26.26 a | 146.6 ab |
| Kentucky 31 Endo+ | 23.96 ab | 142.8 bc |
| Rebel II | 20.23 ca | 142 c |
| Rebel Jr | 17.09 e | 144.5 bc |
| Shortstop | 19.85 d | 145 bc |
| Silverado | 17.88 de | 144.1 bc |
| Torpedo | 25.43 a | 144.3 bc |
| LSD (0.05) | 2.482 | 3.79 |
| Standard Deviation | 1.434 | 2.19 |
| CV | 6.92 | 1.51 |

*The heading date of a plant is the date when two ears are just visible.

TABLE 6

Morphological Measurements of Tall Fescues.

| | Character Rated | | | | |
|---|---|---|---|---|---|
| | Tiller* | Tiller | First Internode | Peduncle | Panicle |
| | | | Rating Data Type | | |
| | Leaf Width | Leaf Length | Length | Length | Height |
| | | | Rating Unit | | |
| Variety | mm | cm | cm | cm | cm |
| Bonsai | 6.54 e | 9.91 e | 12.07 d | 42.13 cd | 57.13 d |
| Bonanza | 10.12 a | 19.55 ab | 19.01 ab | 55.23 ab | 72.54 bc |
| Bar Fa 08PB | 7.93 cd | 17.05 c | 16.42 bc | 44.54 bcd | 73.45 bc |
| Kentucky 31 Endo+ | 10.42 a | 20.26 a | 22.77 a | 57.51 a | 101.9 a |
| Rebel II | 9.31 b | 17.68 bc | 16.81 bc | 51.88 abc | 77.45 b |
| Rebel Jr | 7.78 d | 14.4 d | 11.27 d | 39.37 d | 57.65 d |
| Shortstop | 8.57 c | 16.55 cd | 16.52 bc | 49.68 a–d | 72.87 bc |
| Silverado | 7.93 cd | 14.21 d | 12.92 cd | 43.65 bcd | 67.56 c |
| Torpedo | 7.76 d | 18.81 abc | 16.63 bc | 47.45 a–d | 71.39 bc |
| LSD (0.05) | 0.697 | 2.31 | 4.05 | 10.586 | 8.833 |
| Standard Deviation | 0.403 | 1.335 | 2.34 | 6.115 | 5.103 |
| CV | 4.75 | 8.09 | 14.58 | 12.76 | 7.04 |

*A tiller is a shoot of the plant, formed on the base of the plant.

In mid September 2001, after the seed heads were harvested and above ground foliage was mowed, the amount of rhizome production per plant was measured. Any shoot cluster emerging from the soil and apart from the main plant was counted as one rhizome. The total number of rhizomes per plant was counted. This data was also used to calculate percentage of plants with rhizomes. The distance from edge of the main plant to edge of the rhizome cluster was measured, and the number of shoots in each rhizome cluster counted.

Table 7 shows comparisons of several rhizome characteristics of Bar Fa 08PB with other tall fescue varieties. Statistical analysis was performed as described above. Means followed by same letter do not significantly differ.

TABLE 7

Rhizome Characteristics of Tall Fescues.

| | Character Rated | | | | |
|---|---|---|---|---|---|
| | Rhizome | Rhizome | Rhizome | Shoots | Rhizome |
| | | | Rating Data Type | | |
| | Count | Percent | Shoots | Per rhizome | Length |
| | | | Rating Unit | | |
| Variety | | % | per plant | | cm |
| Bonsai | 0.1 d | 12 e | 1 c | 1 c | 3 f |
| Bonanza | 1.2 b | 66 b | 3 c | 2 bc | 5 cde |
| Bar Fa 08PB | 2.7 a | 88 a | 11 b | 3 b | 11 b |
| Kentucky 31 Endo+ | 0.9 bc | 51 bc | 4 c | 2 bc | 7 c |
| Rebel II | 0.6 cd | 40 cd | 3 c | 2 bc | 4 def |
| Rebel Jr | 0.6 cd | 42 cd | 2 c | 1 c | 4 ef |
| Shortstop | 0.4 cd | 23 de | 3 c | 2 bc | 6 cd |
| Silverado | 0.5 cd | 34 cde | 2 c | 3 bc | 4 ef |
| Torpedo | 3.1 a | 93 a | 15 a | 5 a | 15 a |
| LSD (0.05) | 0.48 | 21 | 3.7 | 1.4 | 1.9 |
| Standard Deviation | 0.28 | 12.1 | 2.1 | 0.8 | 1.1 |
| CV | 24.8 | 24.33 | 42.53 | 34.04 | 16.71 |

Table 8 is a summary of morphological and rhizome characteristics, which the range of values observed shown in parenthesis, of Bar Fa 08PB with other tall fescue varieties. Statistical analysis was performed as described above.

TABLE 8

Range for Measurements of Tall Fescues.

| Character Rated Rating Data Type Rating Unit Variety | Plant Height cm (range) | Rhizome Count number | Rhizome Length cm |
|---|---|---|---|
| Bonsai | 68.06 (12–100.6) | 0.1 (0–2) | 2.7 (1–4) |
| Bonanza | 86.92 (11.6–129.3) | 1.2 (0–5) | 5.3 (1–13) |
| Bar Fa 08PB | 99.66 (27.9–135.3) | 2.7 (0–10) | 11 (1–33) |
| Kentucky 31 Endo+ | 126.69 (49.2–163.4) | 0.9 (0–6) | 6.7 (2–28) |
| Rebel II | 97.53 (30.7–131) | 0.6 (0–5) | 4.3 (1–14) |
| Rebel Jr | 73.82 (45.4–114.2) | 0.6 (0–4) | 4 (2–9) |
| Shortstop | 91.22 (29.8–135.4) | 0.4 (0–5) | 6.1 (1–13) |
| Silverado | 83.9 (7–114.5) | 0.5 (0–3) | 4.6 (2–10) |
| Torpedo | 101.23 (46.4–134.5) | 3.1 (0–12) | 14.7 (1–48) |
| LSD (0.05) | 6.764 | 0.5 | 2.76 |
| Standard Deviation | 18.903 | 1.39 | 7.64 |
| CV | 20.52 | 123.58 | 115.82 |

EXAMPLE 5

Resistance to Rust

The susceptibility of tall fescue to rust (Stem rust, *Puccinia grammis*) was measured as follows. Seeds were grown as described in EXAMPLE 4. Thirty-two weeks after seeding, symptoms of a rust disease (which occurred naturally) were visible. Initial symptoms were visible damage of leaves by rust spores. There were also brown stripes visible on the leaves.

As shown in Table 9, significant difference in rust susceptibility existed among tall fescue entries, with the Bar Fa 08PB variety having a mean disease rating of 8.6 and Silverado having a disease rating of 4.5 (9=no visible symptoms; rating is the mean of three replicates). Means followed by same letter do not significantly differ (P=0.05, Duncan's New MRT).

TABLE 9

Tall fesuce tolerance to Rust.

| Variety | Rust tolerance | |
|---|---|---|
| Bonsai | 6.5 | bc |
| Bonanza | 5.4 | d |
| Bar Fa 08PB | 8.6 | a |
| Kentucky 31 Endo+ | 6.5 | b |
| Rebel II | 5.8 | bcd |
| Rebel Jr | 6.4 | bc |
| Shortstop | 5.8 | cd |
| Silverado | 4.5 | e |
| Torpedo | 8.5 | a |
| LSD (0.05) | 0.65 | |
| Standard Deviation | 0.37 | |
| CV | 5.78 | |

EXAMPLE 6

Endophyte Characterization

Grass samples have the potential to contain endophytic funguses that produce alkaloids. Of the alkaloids produced, lolitrem B and ergovaline can cause animal health problems at certain concentrations. Therefore, Bar Fa 08PB grass samples and seed were analyzed for the presence of endophytes, specifically, for the presence of ergovaline and lolitrem B, using chromatogram analysis. Experimentation was performed by the Oregon State University College of Veterinary Medicine.

To detect lolitrem B and ergovaline alkaloids, fluorometric HPLC assays were conducted. Fescue straw was analyzed as a control. The grass plants were found to have about 55 ppb of ergovaline and <100 ppb of lolitrem B. The seeds had about 183 ppb of ergovaline and <100 ppb of lolitrem B.

Toxicosis due to ergovaline is induced in livestock at the following concentrations: horses, 300–500 ppb; cattle, 400–750 ppb; and sheep, 88–1200+ppb. Toxicosis due to lolitrem B can be seen in livestock at about 1800–2000 ppb. Since Bar Fa 08PB plants only have about 55 ppb of ergovaline and <100 ppb of lolitrem B, and the seeds only 183 ppb ergovaline and <100 ppb of lolitrem B, Bar Fa 08PB grass plants and seeds are not expected to be toxic to livestock.

This data indicates that Bar Fa 08PB is safe for livestock. Therefore, Bar Fa 08PB straw and grass plants can be used in pastures for grazing, and to make hay to feed to livestock.

EXAMPLE 7

Production of Bar Fa 08PB Grasses

Bar Fa 08PB can be grown under normal conditions for growing turf grasses, and bulk seed for large-scale planting can be obtained by methods known in certified seed production. For example, bulk seed may be produced by planting Bar Fa 08PB seeds obtained from either ATCC (Accession No: PTA-3825) or Barenbrug USA, Inc., allowing the mature plants to produce seed by cross-pollination with each other and then collecting the seed. Standard precautions should be taken to prevent cross-pollination from other grasses, such as growing the variety in an isolated plot of sterilized soil, removing adjacent vegetation, etc. The Bar Fa 08PB seeds deposited with ATCC are breeder seeds; propagation of plants from these seeds can be performed under standard conditions known to those skilled in the art.

EXAMPLE 8

Exemplary Uses of Bar Fa 08PB

Bar Fa 08PB can be used in the same way as other tall fescue varieties. However, the high-turf quality and rhizome production affords Bar Fa 08PB particular advantages over other varieties. For example, the use of current commercially available varieties of tall fescue grasses are limited to areas which do not experience extreme high or low temperatures, such as the Southeastern United States. However, Bar Fa 08PB which produces a high-quality turf in subtropical climates and in the southern portion of the transition zone, can be used in such areas. Thus, Bar Fa 08PB is especially marketable and therefore useful.

EXAMPLE 9

Introducing Traits of Bar Fa 08PB Into Other Grass Varieties

The morphological and physiological characteristics of Bar Fa 08PB, including the ability to produce a high-quality turf, can be introduced into other grass varieties by conventional breeding techniques. For example, Bar Fa 08PB can be grown in pollination proximity to another variety of tall fescue grass, allowing cross-pollination to occur between Bar Fa 08PB and the other variety, and then harvesting the hybrid seeds. Plants grown from these hybrid seeds can then be tested for the maintenance of the molecular characteristics described above for Bar Fa 08PB, and/or the plants can simply be observed to see if they display the same growth characteristics described in the above tables.

For example, plants grown from these hybrid seeds can be tested for any of the morphological characteristics described herein, and/or for the production of a high-quality turf. In this way, the high number of rhizomes and high quality turf characteristics may be combined with other desirable plant characteristics. Thus, the provision of Bar Fa 08PB enables the production of progeny plants of Bar Fa 08PB having the rhizome and high quality turf characteristics. "Progeny plants" of Bar Fa 08PB are any plants that are the offspring of a cross between Bar Fa 08PB and any other plant or plants. Progeny plants also include successive generations of the offspring, for example those selected for high-quality turf production using the methods described herein. First-generation progeny plants may retain the high-quality turf production and rhizome characteristics of the Bar Fa 08PB parent. However, if a first-generation progeny plant does not retain the desired level of turf production and rhizomes observed with Bar Fa 08PB, subsequent generations of offspring can be recycled for turf production and rhizomes which have at least the same turf production and rhizome characteristics of Bar Fa 08PB described herein. In one embodiment, subsequent generations of offspring can have a turf quality that exceeds that of Bar Fa 08PB, and/or have more rhizomes than Bar Fa 08PB.

In addition, Bar Fa 08PB can be used as transformation targets for the production of transgenic grasses. In certain embodiments, the present disclosure contemplates the transformation of cells derived from Bar Fa 08PB with at least one transgene. For example, transgenes that can be used, include, but are not limited to, transgenes that confer resistance to herbicides, insect, disease (viral, bacterial, fungal, nematode) or drought resistance, standability, prolificacy, salt damage resistance, and quality are useful. Examples of such genes and methods of transforming plants are described in U.S. Pat. No. 6,025,545 to Lundquist et al., herein incorporated by reference.

Having illustrated and described the principles of the disclosure in multiple embodiments and examples, it should be apparent to those skilled in the art that the disclosure can be modified in arrangement and detail without departing from such principles. The invention, therefore, encompasses all modifications coming within the spirit and scope of the following claims.

I claim:

1. A tall fescue plant, comprising the morphological and physiological properties of a grass plant grown from a seed deposited under American Type Culture Collection (ATOC) No. PTA-3825.

2. Sod, comprising the grass plant of claim 1.
3. Hay, comprising the grass plant of claim 1.
4. Turf, comprising the grass plant of claim 1.
5. The grass plant of claim 1 planted in a golf course fairway.
6. The grass plant of claim 1 planted in a golf course rough.
7. The grass plant of claim 1 planted in a lawn.
8. The grass plant of claim 1 planted in an athletic field.
9. The grass plant of claim 1 planted iii a park.
10. The grass plant of claim 1 planted in a pasture.
11. Progeny of a grass plant according to claim 1, wherein the progeny comprise all of the morphological and physiological properties of a grass plant grown from a seed deposited under American Type Culture Collection (ATOC) No. PTA-4825.

12. Seed of the grass plant of claim 1, wherein the seed produces a grass plant comprising all of the morphological and physiological properties of a grass plant grown from a seed deposited under American Type Culture Collection (ATCC) No. PTA-3825.

13. A seed mixture, comprising the seed of claim, 12.
14. A vegetative sprig or clone of the grass plant of claim 1.
15. A grass plant produced from the grass plant of claim 1 by transformation with a trans gene that confers upon the grass plant resistance to a herbicide.
16. Seed resulting from crossing the grass plant of claim 1 with a second grass plant, wherein the seed produces a grass plant comprising all of the morphological and physiological properties of a grass plant grown from a seed deposited under American Type Culture Collection (ATCC) No. PTA-3825.
17. A grass plant grown from the seed of claim 16, wherein the grass plant comprises all of the morphological and physiological properties of a grass plant grown from a seed deposited under American Type Culture Collection (ATCC) No. PTA-3825.
18. Sod, comprising the grass plant of claim 17.
19. Hay, comprising the grass plant of claim 17.
20. The grass plant of claim 17 planted in a golf course fairway.
21. The grass plant of claim 17 planted in a golf course rough.
22. The grass plant of claim 17 planted in a lawn.
23. The grass plant of claim 17 planted in an athletic field.
24. The grass plant of claim 17 planted in a park.
25. The grass plant of claim 17 planted in a pasture.
26. A method of producing grass seed, comprising planting the grass seed of claim 12 under conditions that result in the germination of the seed, growth of grass plants and setting of progeny seed; and harvesting the progeny seed.

27. Grass seed produced by the method of claim 26, wherein a grass plant grown from the grass seed comprises all of the morphological and physiological properties of a grass plant grown from a seed deposited under American Type Culture Collection (ATCC) No. PTA-3825.
28. A mixture of grass seed comprising the grass seed of claim 27.
29. A method of producing a grass plant, the method comprising:

crossing a first grass plant with at least one other grass plant to produce at least one seed, wherein the first grass plant is the grass of claim 1;

harvesting the seed; and germinating the seed to produce at least one progeny grass plant.

30. A grass plant produced by the method of claim 29, wherein the grass plant comprises all of the morphological and physiological properties of a grass plant grown from a seed deposited under American Type Culture Collection (ATOC) No. PTA-3825.
31. Sod, comprising the grass plant of claim 30.
32. Hay, comprising the grass plant of claim 30.
33. The grass plant of claim 30 planted in a golf course fairway.
34. The grass plant of claim 30 planted in a golf course rough.
35. The grass plant of claim 30 planted in a lawn.

36. The grass plant of claim 30 planted in an athletic field.

37. The grass plant of claim 30 planted in a park.

38. The grass plant of claim 30 planted in a pasture.

39. A vegetative sprig or clone of the grass plant of claim 30.

40. A grass plant produced from the grass plant of claim 31, by transformation with a transgene that confers upon the grass plant resistance to a herbicide.

41. Grass seed deposited as ATCC No: PTA-3825.

42. Turf, comprising a grass plant germinated from the seed of claim 41.

43. Turf, comprising the grass plant of claim 17.

44. Turf, comprising the grass plant of claim 30.

45. Sod, comprising a grass plant germinated from the seed of claim 41, wherein the grass plant comprises all of the morphological and physiological properties of a grass plant grown from a seed deposited under American Type Culture Collection (ATCC) No. PTA-3825.

46. A grass plant germinated from the seed of claim 41, wherein the grass plant comprises all of the morphological and physiological properties of a grass plant grown from a seed deposited under American Type Culture Collection (ATCC) No. PTA-3825.

47. A grass plant produced from the grass plant of claim 1 by transformation with a transgene that confers upon the grass plant resistance to a bacterial disease, viral disease, fungal disease or nematode.

48. A grass plant produced from the grass plant of claim 1 by transformation with a transgene that confers upon the grass plant resistance to an insect.

49. A grass plant produced from the grass plant of claim 1 by transformation with a transgene that confers upon the grass plant drought tolerance.

50. A grass plant produced from the grass plant of claim 1 by transformation with a transgene that confers upon the grass plant salt tolerance.

51. A grass plant produced from the grass plant of claim 30 by transformation with a transgene that confers upon the grass plant resistance to a bacterial disease, viral disease, fungal disease or nematode.

52. A grass plant produced from the grass plant of claim 30 by transformation with a transgene that confers upon the grass plant resistance to an insect.

53. A grass plant produced from the grass plant of claim 30 by transformation with a transgene that confers upon the grass plant drought tolerance.

54. A grass plant produced from the grass plant of claim 30 by transformation with a transgene that confers upon the grass plant salt tolerance.

* * * * *

UNITED STATES PATENT AND TRADEMARK OFFICE
CERTIFICATE OF CORRECTION

PATENT NO. : 6,677,507 B2
DATED : January 13, 2004
INVENTOR(S) : Jacobus de Bruijn It is certified that error appears in the above-identified patent and that said Letters Patent is hereby corrected as shown below:

Column 4,
Line 53, Table 1, "$100^1$" should be -- $100^1$ --.

Column 6,
Line 14, Table 3, "$^d$Jun." should be -- $^d$June --.

Column 11,
Line 53, "(ATOC)" should be -- (ATCC) --.
Line 63, "iii" should be -- in --.

Column 12,
Line 2, "4825" should be -- 3825 --.
Line 8, the comma "," after "claim" should be deleted.

Column 13,
Lines 6-7, "claim 31" should be -- claim 30 --.

Signed and Sealed this

Thirteenth Day of July, 2004

JON W. DUDAS
*Acting Director of the United States Patent and Trademark Office*